US009650203B2

(12) United States Patent
Millar

(10) Patent No.: US 9,650,203 B2
(45) Date of Patent: May 16, 2017

(54) MEDICINAL AEROSOLS AND METHODS OF DELIVERY THEREOF

(71) Applicant: NORTON HEALTHCARE LIMITED, West Yorkshire (GB)

(72) Inventor: Fiona Catherine Millar, Essex (GB)

(73) Assignee: NORTON HEALTHCARE LIMITED, Essex (GB)

( * ) Notice: Subject to any disclaimer, the term of this patent is extended or adjusted under 35 U.S.C. 154(b) by 0 days.

(21) Appl. No.: 14/333,115

(22) Filed: Jul. 16, 2014

(65) Prior Publication Data

US 2014/0326759 A1 Nov. 6, 2014

Related U.S. Application Data

(63) Continuation of application No. 12/455,236, filed on May 29, 2009, now Pat. No. 8,834,849, which is a continuation of application No. 08/999,752, filed on Jun. 4, 1997, now Pat. No. 7,566,445.

(30) Foreign Application Priority Data

Aug. 1, 1996 (GB) .................................. 9616237.5

(51) Int. Cl.
*A61K 9/12* (2006.01)
*B65D 83/14* (2006.01)
*A61K 9/00* (2006.01)
*A61K 47/06* (2006.01)
*B65D 83/54* (2006.01)

(52) U.S. Cl.
CPC ............ *B65D 83/752* (2013.01); *A61K 9/008* (2013.01); *A61K 47/06* (2013.01); *B65D 83/54* (2013.01); *Y10S 514/958* (2013.01)

(58) Field of Classification Search
None
See application file for complete search history.

(56) References Cited

U.S. PATENT DOCUMENTS

| | | | |
|---|---|---|---|
| 2,868,691 A | 1/1959 | Porush | |
| 3,014,844 A | 12/1961 | Thiel | |
| 4,814,161 A | 3/1989 | Jinks | |
| 4,895,719 A | 1/1990 | Radhakrishnan | |
| 5,115,803 A | 5/1992 | Sioutas | |
| 5,118,494 A | 6/1992 | Schultz | |
| 5,225,183 A | 7/1993 | Purewal | |
| 5,348,730 A * | 9/1994 | Greenleaf | A61K 9/008 424/43 |
| 5,355,872 A * | 10/1994 | Riggs | A61M 15/00 128/200.18 |
| 5,376,359 A | 12/1994 | Johnson | |
| 5,605,674 A | 2/1997 | Purewal | |
| 5,653,961 A | 8/1997 | McNally | |
| 5,653,962 A | 8/1997 | Akehurst | |
| 5,674,471 A | 10/1997 | Akehurst | |
| 5,695,743 A | 12/1997 | Purewal | |
| 5,736,124 A * | 4/1998 | Akehurst | A61K 9/008 424/45 |
| 5,766,573 A | 6/1998 | Purewal | |
| 5,891,419 A | 4/1999 | Cutie | |
| 5,899,201 A * | 5/1999 | Schultz | A61M 15/0086 128/200.14 |
| 5,980,867 A | 11/1999 | Tzou | |
| 6,004,537 A | 12/1999 | Blondino | |
| 6,136,294 A | 10/2000 | Adjei | |
| 6,261,539 B1 | 7/2001 | Adjei | |
| 6,352,684 B1 | 3/2002 | Purewal | |
| 6,458,338 B1 | 10/2002 | Adjei | |
| 6,475,467 B1 | 11/2002 | Keller | |
| 6,585,958 B1 | 7/2003 | Keller | |
| 7,566,445 B1 | 7/2009 | Millar | |

FOREIGN PATENT DOCUMENTS

| | | |
|---|---|---|
| AU | 3038197 | 2/1998 |
| CA | 2320129 | 6/1993 |
| CA | 2261879 | 2/1998 |
| CN | 1296814 | 5/2001 |
| EP | 0372777 | 6/1990 |
| EP | 0536235 | 4/1993 |
| EP | 0616525 | 9/1994 |
| EP | 0653205 | 5/1995 |
| EP | 0717987 | 6/1996 |
| EP | 0918507 | 6/1999 |

(Continued)

OTHER PUBLICATIONS

"Aerosol adapter and spray", 1 pg, D18c (submitted in Opposition on Jul. 15, 2006) from Opposition of European Patent Application No. 97925141.0.
ABPI Compendium of Data Sheets and Summaries of Product Characteristics, 1996-97, pp. 566-567.
Clark, A.R., Journal of Biopharmaceutical Sciences, 3(1/2), 1992, 069-076.
Complaints System dated Jul. 3, 1995, 1 pg, D18d from Opposition of European Patent Application No. 97925141.0.
Email between Furlong and MHRA, Feb. 27, 2007, 8 pgs, D24 from Opposition of European Patent Application No. 97925141.0.
Email from Mhra to Furlong, Mar. 28, 2007, 2 pgs, D27 from Opposition of European Patent Application No. 97925141.0.
Entire patent prosecution history of U.S. Appl. No. 08/999,752, filed Jun. 4, 1997, entitled, "Medicinal Aerosols and Methods of Delivery Thereof," now U.S. Pat. No. 7,566,445, issued Jul. 28, 2009.
Entire patent prosecution history of U.S. Appl. No. 12/455,236, filed May 29, 2009, entitled, "Medicinal Aerosols and Methods of Delivery Thereof," now U.S. Pat. No. 8,834,849, issued Sep. 16, 2014.

(Continued)

Primary Examiner — Susan Tran
(74) Attorney, Agent, or Firm — Morgan, Lewis & Bockius LLP

(57) ABSTRACT

The replacement of chlorofluorohydrocarbon propellants in medical aerosols is of the utmost importance to the pharmaceutical industry. A number of formulations have been investigated.
The present invention provides a medical aerosol formulation comprising a particular medicament, a fluorocarbon propellant and 6 to 25% w/w of the total formulation of a polar co-solvent, such formulation being substantially free of surfactant. Canisters suitable for delivering such a pharmaceutical formulation are also provided.

32 Claims, No Drawings

(56) References Cited

FOREIGN PATENT DOCUMENTS

| | | |
|---|---|---|
| EP | 1086688 | 3/2001 |
| ES | 2141049 | 3/2000 |
| NO | 990454 | 3/1999 |
| WO | 9111173 | 8/1991 |
| WO | 9111495 | 8/1991 |
| WO | 9114422 | 10/1991 |
| WO | 9200062 | 1/1992 |
| WO | 9200107 | 1/1992 |
| WO | 9206675 | 4/1992 |
| WO | 9208446 | 5/1992 |
| WO | 9222286 | 12/1992 |
| WO | 9222287 | 12/1992 |
| WO | 9222288 | 12/1992 |
| WO | 9305765 | 4/1993 |
| WO | 9306185 | 4/1993 |
| WO | 9311743 | 6/1993 |
| WO | 9311744 | 6/1993 |
| WO | 9311745 | 6/1993 |
| WO | 9311747 | 6/1993 |
| WO | WO 9311747 A1 * 6/1993 ............. A61K 9/008 |
| WO | 9403153 | 2/1994 |
| WO | 9413262 | 6/1994 |
| WO | 9413263 | 6/1994 |
| WO | 9517195 | 6/1995 |
| WO | 9606598 | 3/1996 |
| WO | 9618384 | 6/1996 |
| WO | 9619198 | 6/1996 |
| WO | 9629985 | 10/1996 |
| WO | 9632345 | 10/1996 |
| WO | 9744012 | 11/1997 |
| WO | 9747286 | 12/1997 |
| WO | 9805302 | 2/1998 |
| WO | 9824420 | 6/1998 |
| WO | 9834595 | 8/1998 |
| WO | 9834596 | 8/1998 |
| WO | 9856349 | 12/1998 |
| WO | 9929296 | 6/1999 |
| WO | 9953901 | 10/1999 |
| WO | 9965460 | 12/1999 |
| WO | 9965464 | 12/1999 |
| WO | 0045795 | 8/2000 |
| WO | 0048587 | 8/2000 |
| WO | 0051591 | 9/2000 |
| WO | 0053187 | 9/2000 |
| WO | 0053188 | 9/2000 |
| WO | 0073170 | 12/2000 |

OTHER PUBLICATIONS

Extract from Ivex website, Oct. 1, 2001, 2 pgs, D26 from Opposition of European Patent Application No. 97925141.0.
Extract from MIMS, Mar. 2007, 2 pgs, D25 from Opposition of European Patent Application No. 97925141.0.
Fink, J.B. Respiratory Care, Jun. 2000, 45(6), pp. 623-635.
International Preliminary Examination Report dated Feb. 26, 1998.
Kennedy, K, Letter from Medicines Control Agency, Mar. 10, 1995, 43 pgs, D18b from Opposition of European Patent Application No. 97925141.0.
Merck Index, Ninth Edition, 1976, p. 30.
MIMS, Jul. 1996, p. 220.
Moore, B., 3M Letter Re: Airomir Inhaler, Apr. 21, 2005, 1 pg, D18a from Opposition of European Patent Application No. 97925141.0.
Ranucci, J.A. et al., Pharmaceutical Technology, Mar. 1992.
The Merck Index, 11th Edition, Merck & Co., Inc., Whitehouse Station, NJ, 1989, cover page + p. 663-664.

* cited by examiner

MEDICINAL AEROSOLS AND METHODS OF DELIVERY THEREOF

CROSS-REFERENCE TO RELATED APPLICATIONS

This application is a continuation of U.S. application Ser. No. 12/455,236, filed May 29, 2009, now U.S. Pat. No. 8,834,849, which is a continuation of application Ser. No. 08/999,752, filed Jun. 4, 1997, now U.S. Pat. No. 7,566,455, which claims priority to Great Britain Application No. 9616237.5, filed Aug. 1, 1996. The disclosure of each of the aforementioned applications is incorporated by reference herein in its entirety for all purposes.

BACKGROUND OF THE INVENTION

This invention relates to pharmaceutical formulations for inhalation aerosols. The Montreal Protocol on ozone depleting gases has made the reformulation of existing pharmaceutical aerosols for inhalation treatment containing chlorofluorohydrocarbon propellants, a matter of urgency for the pharmaceutical industry.

DETAILED DESCRIPTION

A number of hydrofluorocarbons (HFCs) have been the subject to toxicological testing and two in particular P134a (1,1,1,2-tetrafluoroethane) and P227 (1,1,1,2,3,3,3-heptafluoropropane) have been identified as safe for use in pharmaceutical aerosols.

A number of patent applications have been submitted in this field, the first being EP 372777, which discloses the use of four component mixtures, comprising a medicament, a surfactant, P134a and a co-solvent of higher polarity than the P134a, in the form of a solution or a suspension.

As inhalation aerosols are meant for administration to the lung, it has long been accepted that such formulations should contain as few ingredients as possible, to avoid putting unnecessary materials into the lung.

Historically, despite EP 372777, solution aerosols contained only medicament, propellant or propellant mixtures and, if necessary, co-solvent, usually ethanol, eg U.S. Pat. No. 2,868,691. The use of a surfactant was normally unnecessary for solution aerosols. However, historically medicinal suspension aerosols have contained a surfactant eg U.S. Pat. No. 3,014,844, as it was considered that the use of a surfactant was necessary to prevent agglomeration of particles, to prevent adhesion to the sides of the canister, and to aid valve lubrication and prevent valve sticking.

However it was disclosed in EP 616525 that it is possible to prepare medicament suspensions in a hydrofluorocarbon without the need for a surfactant, if a polar co-solvent was added. The normal co-solvent ethanol, has well established physiological actions and being a pure absorbable liquid eliminates any possibility of residues remaining in the lung. Irritation or possible toxicity from the surfactant, many of which are mixtures of similar compounds, are avoided.

EP 616525 specifically limits the polar co-solvent level to 0.01 to 5% w/w and in particular states (page 3, line 55) that the preferred level is about 0.1% w/w.

According to a first aspect of the present invention there is provided a medicinal aerosol formulation comprising a particulate medicament, a fluorocarbon propellant and 6% to 25% w/w of the total formulation of a polar co-solvent, such formulation being substantially free of surfactant.

According to a second aspect of the present invention there is provided a medicinal aerosol formulation, comprising one or more particulate medicaments, one or more fluorocarbon or hydrocarbon or aliphatic gas propellants and 6% to 25% w/w of a polar co-solvent.

According to a third aspect of the present invention there is provided a canister suitable for delivering a pharmaceutical aerosol formulation, which comprises a container capable of withstanding the vapour pressure of the propellant used, which container is closed with a metering valve and contains a pharmaceutical aerosol formulation which comprises particulate medicament, a propellant consisting all or part of fluorocarbon and 6% to 25% of a polar co-solvent, which is substantially free of surfactant.

It has now been surprisingly found that higher levels of alcohol have beneficial results. Levels of 6% or more of ethanol produce satisfactory suspensions, which do not agglomerate on standing, and on reshaking produce finely dispersed medicament. It is believed that the higher levels of alcohol reduce the degree of deposition on the inside of the can. This is a very desirable feature. In addition, the use of these larger percentages of ethanol enables a much cheaper production process.

Medicinal aerosols can be filled either with one dose of liquid containing all of the ingredients mixed together or by a two dose process where the first dose contains the medicament and all other ingredients, including co-solvents, surfactants, if any, ancillary compounds eg flavours, if any, and some times some of the propellant followed by a second dose of pure propellant. This two dose fill has major cost advantages in that the volume of mix for a fixed number of cans is significantly smaller enabling the use of smaller mixing vessels. In particular, with the use of the new HFC propellants, which have lower boiling points than the old CFC propellants, the use of a one dose fill may involve the use of cooled pressurised vessels to prevent evaporation of the propellant gas during mixing and filling. With the new formulations with added extra co-solvent a first mix of just medicament suspended in the co-solvent can be used, followed by a second dose of pure propellant. This means that the propellant can be dosed directly from a holding tank into the can without any need to mix and store with the other ingredients. For example a mix weight of 1 g of medicament and co-solvent can be followed by 7.5 g of propellant. In this way the volume to be mixed is reduced from 8.5 g to 1 g. All the examples in EP 616525 are of laboratory scale, where the handling problems are much easier, but all the formulations described are such that it would not be practicable to fill in two doses without mixing the propellant, as is the case with the present disclosure.

The description of the filling method given on page 5 lines 2-13 indicates that only a one dose filling method is envisaged.

In all cases of the present invention the medicament consists of a particle size suitable for inhalation into the lung and will thus be less than 100 microns, desirably less than 20 microns and preferably in the range of 1-10 microns, normally with a mean particle size 1-5 microns.

Medicaments which may be administered in aerosol formulations according to the invention include any drug useful in inhalation therapy which may be presented in a form which is substantially completely insoluble in the selected propellant.

Appropriate medicaments may thus be selected from, for example, analgesics, eg codeine, dihydromophine, ergotamine, fentanyl or morphine; anginal preparations, eg diltiazem; antiallergics, eg cromoglycate, ketotifen or nedocromil; anti-infectives, eg cephalosporins, penicillins, streptomycin, sulphonamides, tetracyclines and pentamidine; antihistamines, eg methapyrilene; anti-inflammatories, eg beclomethasone, flunisolide, budesonide, tipredane, triamcinolone acetonide or fluticasone; antitussives, eg noscapine; bronchodilators, eg ephedrine, adrenaline, fenoterol, formoterol, isoprenaline, metaproterenol, phenylephrine, phenylpropanolamine, pirbuterol, reproterol, rimiterol, salbutamol, salmeterol, terbutaline, isoetharine, tolubuterol, orciprenaline; diuretics, eg amiloride; anticholinergics, eg ipratropium, atropine or oxitropium; hormones, eg cortisone, hydrocortisone or prednisolone; xanthines, eg aminophylline, choline theophyllinate, lysine theophyllinate or theophylline; and therapeutic proteins and peptides, eg insulin or glucagon. It will be clear to a person skilled in the art that, where appropriate, the medicaments may be used in the form of salts (eg as alkali metal or amine salts or as acid addition salts) or as esters (eg lower alkyl esters) or as solvates (eg hydrates) to optimise the activity and/or stability of the medicament and/or to minimise the solubility of the medicament in the propellant.

Preferred are those compounds which are also substantially insoluble in the co-solvent. Particularly preferred as medicament is salbutamol either as base or as a salt and especially salbutamol sulphate.

Co-solvents may be selected from polar alcohols and polyols, particularly C2-C6 aliphatic alcohols and polyols, such as propylene glycol, and preferably ethanol. Levels of co-solvent will be between 6% and 25% w/w of the total canister content, preferably between 10-15% w/w of canister content.

The propellant may be a hydrofluorocarbon, particularly P134a or P227. Other hydrofluorocarbons or hydrocarbons or aliphatic gases (eg Dimethylether) may be added to modify the propellant characteristics as required.

The product is preferentially produced by weighing the active medicament and suspending it in the co-solvent. The appropriate amount of suspension is then dosed into the can, followed by a second dose of propellant or propellant mix. However, a one shot fill or any other equivalent method may be employed.

The normal medicinal product on the market has an actuator with spray orifice diameter of about 480 microns. However, with the larger percentages of ethanol envisaged in this invention, it is desirable that the co-solvent evaporates from the particles as rapidly as possible.

This is achieved by reducing the aperture to between 100-300 microns, which for the same dosage or drug, gives more rapid evaporation of the co-solvent. A particularly preferred embodiment of the invention is a combination of a level 10-15% co-solvent (normally ethanol) with a stem aperture of 150-250 microns.

The invention is further described by means of example but not in any limitative sense.

EXAMPLE

| | |
|---|---|
| Salbutamol Sulphate | 0.03 g |
| Ethanol | 0.97 g |
| Tetrafluoroethane (P134a) | 7.5 g |

The salbutamol sulphate previously micronised to give over 90% of particles below 10 microns was weighed out and added to the ethanol. The suspension was mixed until is was smooth and uniform and then filled into the aerosol canister. The metering valve assembly was crimped (preferably vacuum crimped) on the canister and then the P134a was filled through the valve. The valve capacity is such as to deliver 100 micrograms of salbutamol, as salbutamol sulphate per actuation.

A particularly preferred use of such a canister is in a patient breath operated device rather than the normal hand operated device. Such devices are available commercially such as those under the trade mark "Easi-Breathe".

The invention claimed is:

1. A method of making a product suitable for delivering a pharmaceutical aerosol formulation, the method comprising the steps of:
    a) forming a suspension by adding a bronchodilator selected from the group consisting of ephedrine, adrenaline, fenoterol, formoterol, isoprenaline, metaproterenol, phenylephrine, phenylpropanolamine, pirbuterol, reproterol, rimiterol, salbutamol, salmeterol, terbutaline, isoetharine, tolubuterol and orciprenaline, or a salt of said bronchodilator to at least one polar co-solvent followed by mixing, and then dosing the suspension into a canister;
    b) dosing at least one propellant selected from the group consisting of fluorocarbon propellants, hydrocarbon propellants and aliphatic gas propellants into the canister to form the pharmaceutical aerosol formulation; and
    c) combining the canister with an actuator having a spray orifice aperture of from 100 to 300 microns;
        wherein the pharmaceutical aerosol formulation is comprised of 6% to 25% w/w of polar co-solvent.

2. The method of claim 1, wherein the bronchodilator is substantially insoluble in the at least one polar co-solvent.

3. The method of claim 1, wherein the at least one propellant is a hydrofluorocarbon.

4. The method of claim 1, wherein the at least one propellant is 1,1,1,2-tetrafluoroethane or 1,1,1,2,3,3,3-heptafluoro-n-propane.

5. The method of claim 1, wherein the bronchodilator is a salt of salbutamol.

6. The method of claim 1, wherein the at least one polar co-solvent is selected from the group consisting of C2-C6 aliphatic alcohols and polyols.

7. The method of claim 1, wherein the at least one polar co-solvent is ethanol.

8. The method of claim 1, wherein the pharmaceutical aerosol formulation is substantially free of surfactant.

9. The method of claim 1, wherein the spray orifice aperture is from 150 to 250 microns.

10. The method of claim 1, wherein the bronchodilator has a particle size of less than 20 microns.

11. The method of claim 1, wherein the actuator is a breath activated device.

12. The method of claim 1, wherein the bronchodilator is micronized prior to step a).

13. The method of claim 1, wherein the canister is closed with a metering valve.

14. The method of claim 13, wherein the at least one propellant is dosed through the metering valve.

15. A method of making a product suitable for delivering a pharmaceutical aerosol formulation, the method comprising the steps of:
    a) forming a suspension by adding salbutamol or a salt thereof to ethanol followed by mixing, and then dosing the suspension into a canister;
    b) dosing 1,14,2-tetrafluoroethane or 1,1,1,2,3,3,3-heptafluoro-n-propane into the canister to form the pharmaceutical aerosol formulation, which is substantially free of surfactant and which is comprised of 10% to 15% w/w ethanol; and c) combining the canister with an actuator having a spray orifice aperture of from 150 to 250 microns.

16. The method of claim 15, wherein salbutamol sulphate is used in step a).

17. The method of claim 16, wherein the salbutamol sulphate has a particle size of less than 20 microns.

18. The method of claim 15, wherein the canister is closed with a metering valve and the metering valve has a capacity such as to deliver 100 micrograms of salbutamol, as salbutamol sulphate, per actuation.

19. The method of claim 15, wherein the salbutamol or salt thereof is micronized prior to step a).

20. The method of claim 15, wherein the canister is closed with a metering valve and the 1,1,1,2-tetrafluoroethane or 1,1,1,2,3,3,3-heptafluoro-n-propane is filled into the canister through the metering valve.

21. A method of making a canister containing a pharmaceutical aerosol formulation, wherein the method comprises the steps of:

a) forming a suspension by adding a bronchodilator selected from the group consisting of ephedrine, adrenaline, fenoterol, formoterol, isoprenaline, metaproterenol, phenylephrine, phenylpropanolamine, pirbuterol, reproterol, rimiterol, salbutamol, salmeterol, terbutaline, isoetharine, tolubuterol and orciprenaline, or a salt of said bronchodilator to at least one polar co-solvent followed by mixing, and then dosing the suspension into a canister; and b) dosing at least one propellant selected from the group consisting of fluorocarbon propellants, hydrocarbon propellants and aliphatic gas propellants into the canister to form the pharmaceutical aerosol formulation, wherein the pharmaceutical aerosol formulation is comprised of 6% to 25% w/w of polar co-solvent.

22. The method of claim 21, wherein the bronchodilator is substantially insoluble in the at least one polar co-solvent.

23. The method of claim 21, wherein the at least one propellant is a hydrofluorocarbon.

24. The method of claim 21, wherein the at least one propellant is 1,1,1,2-tetrafluoroethane or 1,1,1,2,3,3,3-heptafluoro-n-propane.

25. The method of claim 21, wherein the bronchodilator is a salt of salbutamol.

26. The method of claim 21, wherein the at least one polar co-solvent is selected from the group consisting of C2-C6 aliphatic alcohols and polyols.

27. The method of claim 21, wherein the at least one polar co-solvent is ethanol.

28. The method of claim 21, wherein the pharmaceutical aerosol formulation is substantially free of surfactant.

29. The method of claim 21, wherein the bronchodilator has a particle size of less than 20 microns.

30. The method of claim 21, wherein the bronchodilator is micronized prior to step a).

31. The method of claim 21, wherein the canister is closed with a metering valve.

32. The method of claim 31, wherein the at least one propellant is dosed through the metering valve.

* * * * *